United States Patent
Ohri et al.

(10) Patent No.: US 9,526,568 B2
(45) Date of Patent: Dec. 27, 2016

(54) DRUG-DELIVERY DEVICE FOR USE WITH ABLATION DEVICE

(71) Applicant: COVIDIEN LP, Mansfield, MA (US)

(72) Inventors: Rachit Ohri, Framingham, MA (US); Lan Pham, Nashua, NH (US); Phillip D. Blaskovich, Salem, MA (US); Les Hull, Attleboro, MA (US); Rupal Ayer, Boulder, CO (US); Stephen H. Wu, Chesterfield, MO (US); Clifford J. Herman, Saint Louis, MO (US); William H. Nau, Jr., Longmont, CO (US); Francesca Rossetto, Longmont, CO (US); Allison Waller, Blackstone, MA (US); Wenxing Huang, Shanghai (CN); Paul Dicarlo, Middelboro, MA (US)

(73) Assignee: COVIDIEN LP, Mansfield, MA (US)

( * ) Notice: Subject to any disclaimer, the term of this patent is extended or adjusted under 35 U.S.C. 154(b) by 135 days.

(21) Appl. No.: 14/011,438

(22) Filed: Aug. 27, 2013

(65) Prior Publication Data

US 2015/0065944 A1 Mar. 5, 2015

(51) Int. Cl.
*A61B 18/14* (2006.01)
*A61B 10/02* (2006.01)
(Continued)

(52) U.S. Cl.
CPC ....... *A61B 18/1477* (2013.01); *A61B 10/0233* (2013.01); *A61B 10/06* (2013.01);
(Continued)

(58) Field of Classification Search
CPC . A61M 5/48; A61M 5/482; A61B 2018/0057; A61B 2018/00577; A61B 2018/00011; A61B 18/18; A61B 1/1815
See application file for complete search history.

(56) References Cited

U.S. PATENT DOCUMENTS

D223,367 S  4/1972 Kountz
D263,020 S  2/1982 Rau, III
(Continued)

FOREIGN PATENT DOCUMENTS

CN  1103807  6/1995
DE  390937  3/1924
(Continued)

OTHER PUBLICATIONS

U.S. Appl. No. 13/419,981, filed Mar. 14, 2012, Joseph D. Brannan.
(Continued)

*Primary Examiner* — Imani Hayman
*Assistant Examiner* — Nilay Shah (57) ABSTRACT

A drug-delivery device includes a body configured for attachment to a handle of an ablation device, a shaft portion defining a passageway therein, and a delivery lumen to provide for drug delivery to tissue. The body includes a proximal portion, a distal portion, and a contoured portion disposed therebetween. The contoured portion is configured for engagement with a contoured portion of the handle of the ablation device. The shaft portion includes a proximal end and a distal end. The proximal end of the shaft engages with an opening defined in the distal end of the body. The passageway of the shaft portion is configured to receive the delivery lumen slideably moveably therein. The delivery lumen includes a proximal portion and a distal portion. The drug-delivery device also includes a knob member coupled to the proximal portion of the delivery lumen.

4 Claims, 6 Drawing Sheets

(51) Int. Cl.
*A61M 5/158* (2006.01)
*A61B 10/06* (2006.01)
*A61M 37/00* (2006.01)
*A61B 18/18* (2006.01)
*A61M 5/48* (2006.01)
*A61B 18/00* (2006.01)

(52) U.S. Cl.
CPC ............ *A61M 5/158* (2013.01); *A61M 37/00* (2013.01); *A61B 18/18* (2013.01); *A61B 18/1815* (2013.01); *A61B 2018/00011* (2013.01); *A61B 2018/00029* (2013.01); *A61B 2018/00577* (2013.01); *A61B 2018/00946* (2013.01); *A61B 2018/143* (2013.01); *A61B 2018/1475* (2013.01); *A61M 5/48* (2013.01)

(56) References Cited

U.S. PATENT DOCUMENTS

| | | |
|---|---|---|
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| D354,218 S | 1/1995 | Van de Peer |
| 5,403,311 A | 4/1995 | Abele et al. |
| 5,472,441 A | 12/1995 | Edwards et al. |
| 5,921,982 A | 7/1999 | Lesh et al. |
| 6,016,452 A | 1/2000 | Kasevich |
| D424,693 S | 5/2000 | Pruter |
| D424,694 S | 5/2000 | Tetzlaff et al. |
| D425,201 S | 5/2000 | Tetzlaff et al. |
| 6,176,856 B1 | 1/2001 | Jandak et al. |
| D449,886 S | 10/2001 | Tetzlaff et al. |
| D457,958 S | 5/2002 | Dycus et al. |
| D457,959 S | 5/2002 | Tetzlaff et al. |
| 6,402,742 B1 | 6/2002 | Blewett et al. |
| 6,477,426 B1 | 11/2002 | Fenn et al. |
| 6,478,793 B1 | 11/2002 | Cosman et al. |
| 6,673,070 B2 | 1/2004 | Edwards et al. |
| D487,039 S | 2/2004 | Webster et al. |
| 6,788,977 B2 | 9/2004 | Fenn et al. |
| D496,997 S | 10/2004 | Dycus et al. |
| D499,181 S | 11/2004 | Dycus et al. |
| 7,025,765 B2 | 4/2006 | Balbierz et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| 7,160,296 B2* | 1/2007 | Pearson ............ A61B 18/1477 606/42 |
| D541,418 S | 4/2007 | Schechter et al. |
| D541,938 S | 5/2007 | Kerr et al |
| D564,662 S | 3/2008 | Moses et al. |
| 7,393,352 B2 | 7/2008 | Berube |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| 7,842,076 B2 | 11/2010 | Zikorus et al. |
| D634,010 S | 3/2011 | DeCarlo |
| 7,918,852 B2 | 4/2011 | Tullis et al. |
| 8,079,982 B1* | 12/2011 | Ponzi et al. ............ 604/115 |
| 8,172,757 B2 | 5/2012 | Jaffe et al. |
| D681,810 S | 5/2013 | Decarlo |
| 2002/0120260 A1 | 8/2002 | Morris et al. |
| 2006/0041243 A1 | 2/2006 | Nayak et al. |
| 2006/0079887 A1* | 4/2006 | Buysse et al. ............ 606/41 |
| 2006/0241576 A1 | 10/2006 | Diederich et al. |
| 2007/0073248 A1 | 3/2007 | Moenning |
| 2007/0244529 A1 | 10/2007 | Choi et al. |
| 2007/0270789 A1 | 11/2007 | Berger |
| 2007/0287996 A1 | 12/2007 | Rioux |
| 2009/0149850 A1 | 6/2009 | Turovskiy et al. |
| 2010/0057078 A1* | 3/2010 | Arts ............ A61B 10/06 606/41 |
| 2010/0125269 A1 | 5/2010 | Emmons et al. |
| 2011/0077644 A1 | 3/2011 | Pham et al. |
| 2013/0085487 A1 | 4/2013 | Temelli et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712326 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |

(56) References Cited

FOREIGN PATENT DOCUMENTS

| JP | 2000342599 | 12/2000 |
|---|---|---|
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| KR | 20070093068 | 9/2007 |
| KR | 20100014406 | 2/2010 |
| KR | 20120055063 | 5/2012 |
| SU | 166452 | 11/1964 |
| SU | 401367 | 11/1974 |
| SU | 727201 | 4/1980 |
| WO | 95/22285 A1 | 8/1995 |
| WO | 9904710 A1 | 2/1999 |
| WO | 0012010 A1 | 3/2000 |
| WO | WO00/36985 | 6/2000 |
| WO | 01/08573 A2 | 2/2001 |
| WO | 01/74252 A2 | 10/2001 |
| WO | 2006/105121 A2 | 10/2006 |
| WO | 2006/138719 A2 | 12/2006 |
| WO | 2008/144341 A1 | 11/2008 |
| WO | WO2009/065058 | 5/2009 |
| WO | WO2010/035831 | 4/2010 |

OTHER PUBLICATIONS

U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T, Lo, S.W. Lee.
Carbonell et al., "Comparison of the Gyms PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.

(56) References Cited

OTHER PUBLICATIONS

E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/ Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: Targis™ Technology, "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report dated Sep. 26, 2013 for EP 13 17 0016.
European Search Report for EP 14173860 dated Mar. 9, 2015.

\* cited by examiner

DRUG-DELIVERY DEVICE FOR USE WITH ABLATION DEVICE

CROSS-REFERENCE TO RELATED APPLICATIONS

The present application claims priority to, and the benefit of, U.S. Provisional Application Ser. No. 61/653,804, filed on May 31, 2012, and U.S. Provisional Application Ser. No. 61/658,577, filed on Jun. 12, 2012, the disclosures of which are herein incorporated by reference in their entireties.

BACKGROUND

1. Technical Field

The present disclosure relates to electrosurgical systems and devices for performing medical procedures. The present disclosure relates to the administration of beneficial agents in general, which include any physiologically, pharmacologically active and/or psychotropic substance(s). More particularly, the present disclosure relates to drug-delivery devices for use with ablation devices and electrosurgical systems including the same.

2. Discussion of Related Art

Electrosurgical instruments have become widely used by surgeons. Electrosurgery involves the application of thermal and/or electrical energy to cut, dissect, ablate, coagulate, cauterize, seal or otherwise treat biological tissue during a surgical procedure. Electrosurgery is typically performed using a handpiece including a surgical instrument (e.g., end effector, ablation probe, or electrode) adapted to transmit energy to a tissue site during electrosurgical procedures, an electrosurgical generator operable to output energy, and a cable assembly operatively connecting the surgical instrument to the generator.

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying various forms of energy (e.g., electromagnetic, ultrasonic, etc.) to heat, ablate and/or coagulate tissue. Microwave or radio-frequency energy is sometimes utilized to perform these methods. Radio-frequency (RF) and microwave (MW) energy are electromagnetic radiation in the frequency ranges of 3 kilohertz (kHz) to 300 Megahertz (MHz), and 300 MHz to 300 gigahertz (GHz), respectively. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode (usually a plate positioned on the patient's thigh or back) as the means to complete the electrical circuit between the electrosurgical generator and the patient. In bipolar electrosurgery, the electrosurgical device includes two electrodes that are located in proximity to one another for the application of current between their surfaces. Bipolar electrosurgical current travels from one electrode, through the intervening tissue to the other electrode to complete the electrical circuit.

The benefits provided by controlled delivery of active agents for the treatment of injury or disease are well recognized in the art and various approaches have been taken to realize the goal of delivering active agents at desired rates over predetermined periods of time. Various different implantable controlled delivery formulations are known in the art, and various different mechanisms have been employed for delivering active agent from implantable formulations at a controlled rate over time.

Medical imaging has become a significant component in the clinical setting and in basic physiology and biology research, e.g., due to enhanced spatial resolution, accuracy and contrast mechanisms that have been made widely available. Medical imaging now incorporates a wide variety of modalities, e.g., computed tomography (CT) and magnetic resonance imaging (MRI), that noninvasively capture the structure and/or function of the human body. Such images are acquired and used in many different ways including medical images for diagnosis, staging and therapeutic management of malignant disease.

Medical image processing, analysis and visualization play an increasingly useful role in disease diagnosis and monitoring as well as, among other things, surgical planning and monitoring of therapeutic procedures. A contrast agent may be used for enhancement of the contrast of structures or fluids within the body (or region of interest) in medical imaging to allow visualization and evaluation of lesions seen minimally, if at all, with imaging alone. There is a continuing need for devices capable of dispensing a contrast agent to enhance the visualization of the lesion during the procedure.

Despite advancements in the use of electrosurgical devices for treating biological tissue, there are still concerns for tumor reoccurrence. A continuing need exists for devices capable of dispensing a controlled delivery formulation of a desired active agent, which may help to reduce or eliminate tumor reoccurrence.

SUMMARY

There is a need for drug-delivery devices configured for attachment to ablation devices to provide the capability of dispensing a controlled delivery formulation of a desired active agent (and/or contrast agent). There is a need for drug-delivery devices configured for attachment to energy-delivery devices to provide the capability of dispensing therapeutic agents, e.g., visualization agents, radioactive agents, and/or radiation-protective agents. The combination of ablation (e.g., RF ablation and/or microwave ablation) and drug delivery may help to reduce or eliminate tumor reoccurrence. The combination of ablation and contrast agent introduction may help to enhance the visualization of the lesion during the treatment procedure. There is a need for drug-delivery devices configured for attachment to ablation devices to provide the capability of dispensing a therapeutic agent and/or an active agent in a controlled delivery formulation and/or non-active agent (e.g., contrast agent) before, during and/or after ablation, e.g., without the need for further manipulation of the device.

Electromagnetic energy is generally classified by increasing energy or decreasing wavelength into radio waves, microwaves, infrared, visible light, ultraviolet, X-rays and gamma-rays. As it is used in this description, "ablation procedure" generally refers to any ablation procedure, such as, for example, microwave ablation, radio frequency (RF) ablation or microwave ablation-assisted resection.

As it is used in this description, "energy-delivery device" generally refers to any device that can be used to transfer energy from a power generating source, such as a microwave or RF electrosurgical generator, to tissue. For the purposes herein, the term "ablation device" is interchangeable with the term "energy-delivery device." As it is used in this description, "transmission line" generally refers to any transmission medium that can be used for the propagation of signals from one point to another.

For the purposes of this description, the terms "drug," "drug agent," "implantable drug agent," "active agent," "beneficial agent," "therapeutic agent," "therapeutic molecule," and the like are used interchangeably herein, and may include, for example, small molecules, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species. Some examples of drug agents that may be delivered by devices according to embodiments of the present disclosure are provided later in this description.

According to an aspect of the present disclosure, a drug-delivery device is provided. The drug-delivery device includes a body configured for attachment to a handle of an ablation device, a shaft portion defining a passageway therein, and a delivery lumen to provide for drug delivery to tissue. The body includes a proximal portion, a distal portion, and a contoured portion disposed therebetween. The contoured portion is configured for engagement with a contoured portion of the handle of the ablation device. The shaft portion includes a proximal end and a distal end. The proximal end of the shaft engages with an opening defined in the distal end of the body. The passageway of the shaft portion is configured to receive the delivery lumen slideably moveably therein. The delivery lumen includes a proximal portion and a distal portion. The drug-delivery device also includes a knob member coupled to the proximal portion of the delivery lumen.

According to an aspect of the present disclosure, an electrosurgical system is provided. The electrosurgical system includes an ablation device and a drug-delivery device. The ablation device includes a handle portion and a plurality of ablation electrodes operatively connected to the handle portion. The handle portion includes a contoured portion. The drug-delivery device includes a body, a delivery lumen to provide for drug delivery to tissue, and a knob member. The body is configured for attachment to the handle portion of the ablation device. The body includes a proximal portion, a distal portion, and a contoured portion disposed therebetween. The contoured portion of the body is configured for engagement with the contoured portion of the handle portion of the ablation device. The shaft portion defines a passageway therein. The shaft portion includes a proximal end and a distal end. The proximal end of the shaft engages with an opening defined in the distal end of the body. The delivery lumen includes a proximal portion and a distal portion. The knob member is coupled to the proximal portion of the delivery lumen. The passageway of the shaft portion is configured to receive the delivery lumen slideably moveably therein.

BRIEF DESCRIPTION OF THE DRAWINGS

Objects and features of the presently-disclosed drug-delivery devices for use with ablation devices and electrosurgical systems including the same will become apparent to those of ordinary skill in the art when descriptions of various embodiments thereof are read with reference to the accompanying drawings, of which.

DETAILED DESCRIPTION

Hereinafter, embodiments of the presently-disclosed drug-delivery devices for use with ablation devices, and electrosurgical systems including the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide drug-delivery devices configured to be attachable to energy-delivery devices. Embodiments may be suitable for use with Cool-tip™ RF ablation devices. Embodiments may be suitable for use with microwave ablation devices. Embodiments may be suitable for utilization with endoscopic and laparoscopic surgical procedures. Embodiments may be implemented using electromagnetic radiation at microwave frequencies, RF frequencies or at other frequencies.

Various embodiments of the present disclosure provide electrosurgical system including a drug-delivery device configured to be attachable to an energy-delivery. Various embodiments of the presently-disclosed drug-delivery device include an elongated shaft portion configured to facilitate delivery of one or more drug agents and/or therapeutic agents, which may be temperature sensitive, into tissue. Any suitable number of the same or different drugs may be utilized, e.g., depending upon a particular purpose and/or to achieve a desired surgical outcome. The presently-disclosed drug-delivery device embodiments may be configured for visualization, e.g., configured to allow for delivery of a miniaturized camera system at the distal end of the delivery lumen. The presently-disclosed drug-delivery device embodiments may be configured to allow for delivery of pill-sized cameras.

Drug agents which may be delivered by devices according to embodiments of the present disclosure include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Some examples of implantable drug agents which may be delivered by devices according to embodiments of the present disclosure are provided later in this description. Therapeutic agents which may be delivered by devices according to embodiments of the present disclosure include visualization agents, radio-active agents, and radiation-protective agents. Therapeutic agents need not necessarily be in molecular form (e.g., ethanol may be preferred over molecular therapeutics to induce cytotoxicity for the tumorous tissue). The therapeutic agent and/or formulation may or may not have controlled-release or sustained-release, and may instead be delivered as a bolus.

Various embodiments of the present disclosure provide a "clip-on" component for drug-delivery suitable for use with an ablation device, wherein the device architecture, configuration, and manufacturing process for the ablation device does not need to be modified. Various embodiments of the presently-disclosed "clip-on" component for drug-delivery provide the capability to deliver localized drugs or other payload for therapeutic and/or visualization purposes.

Figure 1:
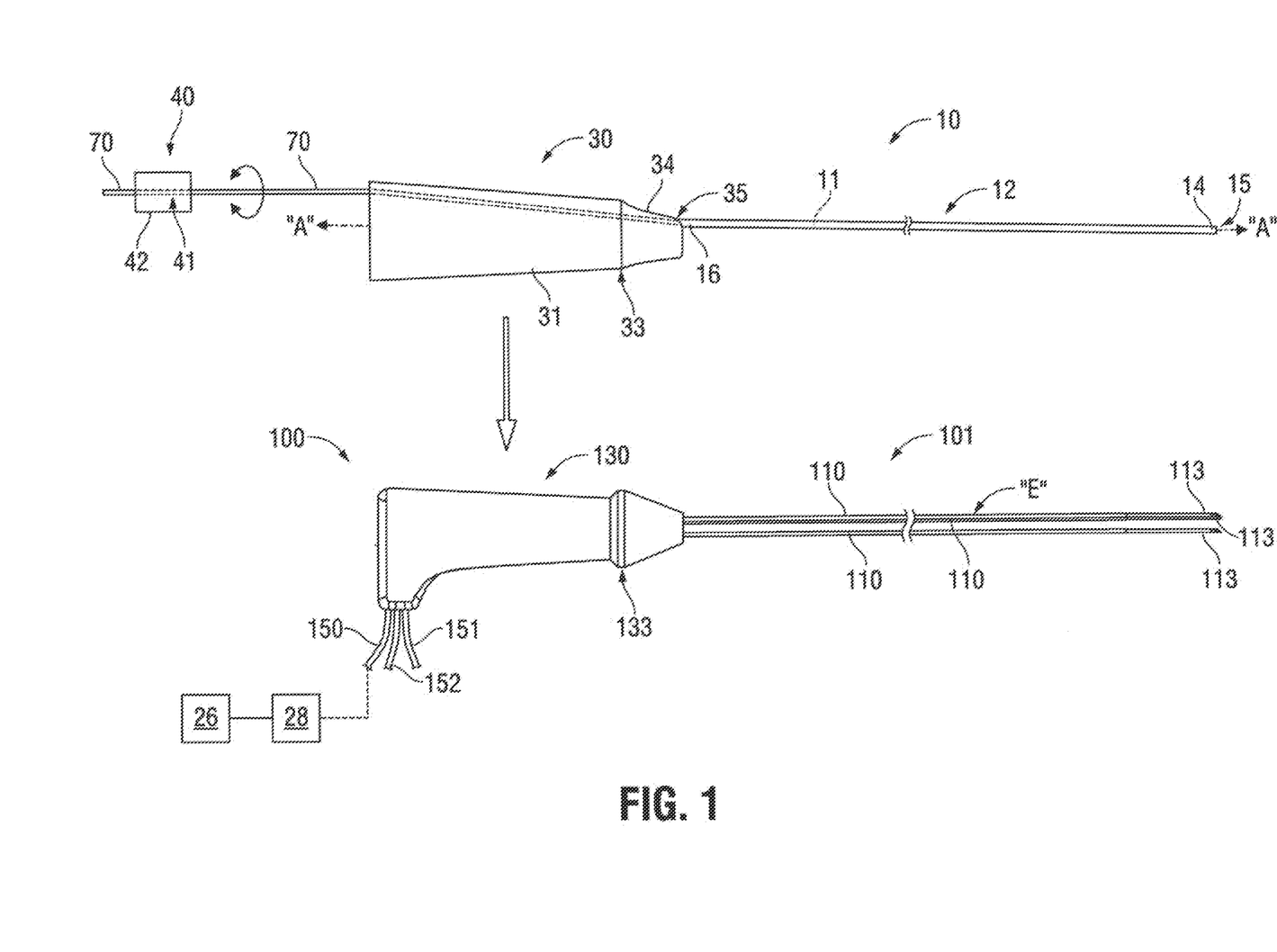
FIG. 1 is a schematic view of a drug-delivery device in an aligned position with respect to an energy-delivery device, spaced apart therefrom, the drug-delivery device including a drug-delivery lumen, a knob member coupled thereto, and a body configured to be attachable to the energy-delivery device, in accordance with an embodiment of the present disclosure.

FIG. 1 shows a drug-delivery device (shown generally as 10) in accordance with an embodiment of the present disclosure and an electrosurgical system (shown generally as 100) including an ablation device 101. Drug-delivery device 10, which is described in more detail later in this description, is adapted to allow the user to selectively position a delivery lumen 70, e.g., for the delivery of therapeutic agents, active pharmaceutical ingredients (APIs), and/or contrast agent, in tissue. The delivery lumen 70 may be either disposable or reusable.

Ablation device 101 includes an electrode array "E" and a handle assembly 130. Electrode array "E" may include one or more ablation electrodes 110. In some embodiments, as shown in FIG. 1, the electrode array "E" includes three ablation electrodes 110 supported on and/or operatively connected to the handle assembly 130. The shape, size and number of ablation electrodes 110 of the electrode array "E" may be varied from the configuration depicted in FIG. 1.

Ablation device 101 is operatively connected via a transmission line 150 to an electrosurgical power generating source 28, e.g., a microwave or radio frequency (RF) electrosurgical generator. Power generating source 28 may be any generator suitable for use with electrosurgical devices and may be configured to provide various frequencies of energy. In some embodiments, ablation device 101 is disposed in fluid communication with a coolant source (not shown). Ablation device 101 may include first and second conduits 151 and 152, respectively, to provide a first fluid-flow path, e.g., leading to the ablation electrodes 110, and a second fluid-flow path, e.g., leading away from the ablation electrodes 110, configured to provide fluid flow of a coolant fluid e.g., deionized water, or other suitable cooling medium, for cooling at least the distal end portion 113 of the ablation electrodes 110. Ablation device 101 may include additional, fewer, or different components than shown in FIG. 1, depending upon a particular purpose or to achieve a desired result.

In some embodiments, electrosurgical system 100 (also referred to herein as ablation system 100) may include a controller 26 for controlling and/or monitoring the operating parameters of the ablation system 100. In some embodiments, as shown in FIG. 1, the controller 26 is communicatively-coupled to the electrosurgical power generating source 28. Controller 26 may include any type of computing device, computational circuit, or any type of processor or processing circuit capable of executing a series of instructions that are stored in a memory (not shown) associated with the controller 26. Functions of the controller 26 may be integrated with those of the electrosurgical power generating source 28 and/or may be integrated with other components of the electrosurgical system 100.

In some embodiments, a drug and/or contrast agent supply line (not shown) may be provided to fluidly-couple the drug-delivery device 10 to a source of the drug and/or contrast agent delivery supply for supplying drugs and/or contrast agent to the delivery lumen 70. A fluid-movement device may be fluidly coupled between the source of the drug (and/or contrast agent) and the delivery lumen 70, and the controller 26 may be communicatively-coupled to the fluid-movement device. In some embodiments, the controller 26 may be configured to control operation(s) of the fluid-movement device, e.g., during an ablation procedure based on one or more operating parameters of the electrosurgical power generating source 28. Electrosurgical system 100 may additionally, or alternatively, include an imaging system (not shown) capable of generating image data, and the controller 26 may be communicatively-coupled to the imaging system. In some embodiments, the controller 26 may be configured to control operation(s) of the fluid-movement device based, at least in part, on data captured by the imaging system.

Drug-delivery device 10 includes an elongated, substantially cylindrically-shaped shaft portion 12 defining a passageway 11 of generally tubular shape configured to receive the delivery lumen 70 slideably moveably therein. Shaft portion 12 generally includes a distal end portion 14 and a proximal end portion 16. A port 15 is located at the distal-most tip of the distal end portion 14. The proximal end portion 16 of the shaft portion 12 engages with an opening 35 defined in the distal portion 34 of the body 30. Although the passageway 11 is generally tubular-shaped, other shapes can be used depending on the configuration of the shaft portion 12. Shaft portion 12 may be formed of any suitable rigid material, and may be either disposable or reusable.

Figure 5:
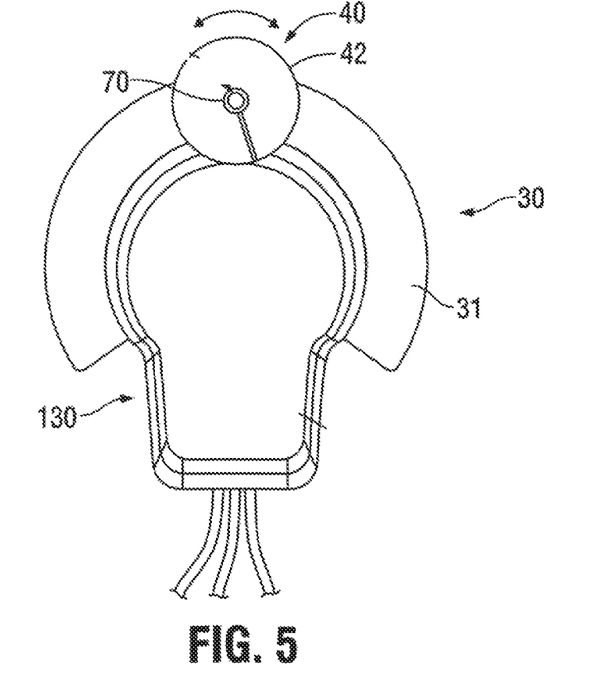
FIG. 5 is a rear, schematic view of the drug-delivery device of FIG. 2 coupled to an energy-delivery device, in accordance with an embodiment of the present disclosure.

Drug-delivery device 10 includes an actuator 40 operatively coupled to the delivery lumen 70. In some embodiments, the actuator 40 includes a knob member 42. In some embodiments, as seen in FIGS. 1 and 5, the knob member 42 defines a channel 41 configured to receive the delivery lumen 70 therethrough. As shown in FIG. 1, the delivery lumen 70 is rotatable about a longitudinal axis "A-A" defined through shaft 12, either manually or otherwise, by the rotatable knob member 42. Actuator 40 may additionally, or alternatively, include a device, e.g., an electric motor, capable of reciprocally moving the delivery lumen 70. In some embodiments, the controller 26 may be configured to control operation(s) of the device, e.g., during an ablation procedure based on one or more operating parameters of the electrosurgical power generating source 28.

Drug-delivery device 10 is configured to allow the user to selectively position the delivery lumen 70, or portion thereof, from within the shaft portion 12 of the drug-delivery device 10 to outside the shaft portion 12. For ease of explanation and understanding, the delivery lumen 70 is described below as selectively positionable with respect to fixed structures, or portions thereof, of the ablation device 101, e.g., in relation to the distal end portion 113 of the ablation electrodes 110, and/or in relation to the distal end 14 of the shaft portion 12 of the drug-delivery device 10.

Figure 3:
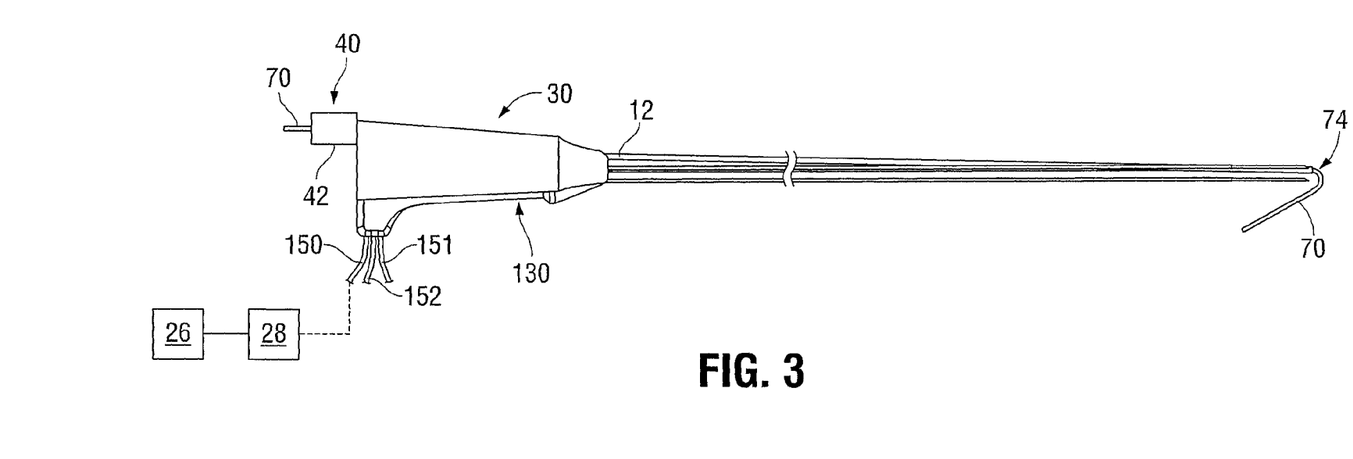
FIG. 3 is a schematic view of the drug-delivery device of FIG. 1 coupled to an energy-delivery device, such as the energy-delivery device of FIG. 1, showing the drug-delivery device in a first configuration in which the knob member thereof is disposed in the distal-most position, wherein the drug-delivery lumen is configured in an extended position, in accordance with an embodiment of the present disclosure.
Figure 6:
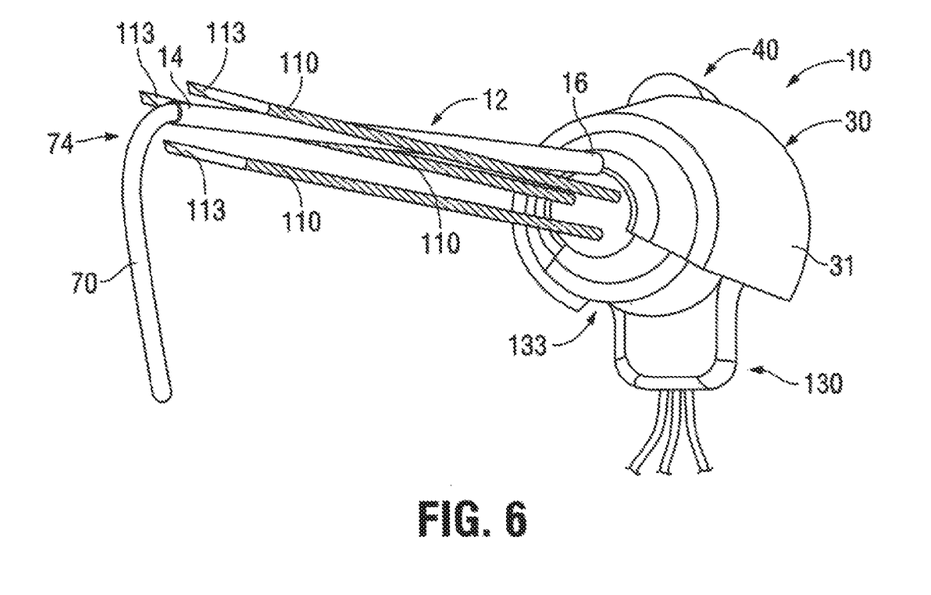
FIG. 6 is a side, perspective view of the drug-delivery device of FIG. 2 coupled to an energy-delivery device, including the drug-delivery lumen shown in an extended position, in accordance with an embodiment of the present disclosure.

Delivery lumen 70 may be formed of any suitable material, and may include one or more portions formed of a flexible material. In some embodiments, as shown in FIGS. 3 and 6, the distal portion 74 of the delivery lumen 70 is formed of a flexible material configured to bend in a curvilinear fashion. The curved or "bent" distal portion 74 of the delivery lumen 70 allows for maneuverability and access in and around the tumor and/or the tumor-margin in a manner suitable for drug-delivery through the delivery lumen 70. In some procedures, the distal portion 74 of the delivery lumen 70 is that portion of the delivery lumen 70 intended to be inserted into the tumor. The dimensions and/or the angle of the bend at the distal portion 74 of the delivery lumen 70, which is rotatably moveable about a longitudinal axis "A-A" (FIG. 1) defined by the shaft portion 12 (shown in FIG. 1), may be selected to enhance the maneuverability of the distal end of the delivery lumen 70. In some embodiments, the distal portion 74 of the delivery lumen 70 may be formed of a shape-memory material. For example, shape-memory alloys may be used to induce a certain angle of the bend at body temperature when delivery lumen 70 is deployed.

In some embodiments, where the delivery lumen 70 is disposable, replaceable and/or interchangeable, different configurations of the delivery lumen 70 (e.g., varied dimensions and angles for the distal end) may be used depending upon the needs of the procedure and/or the preference of the surgeon.

Figure 2:
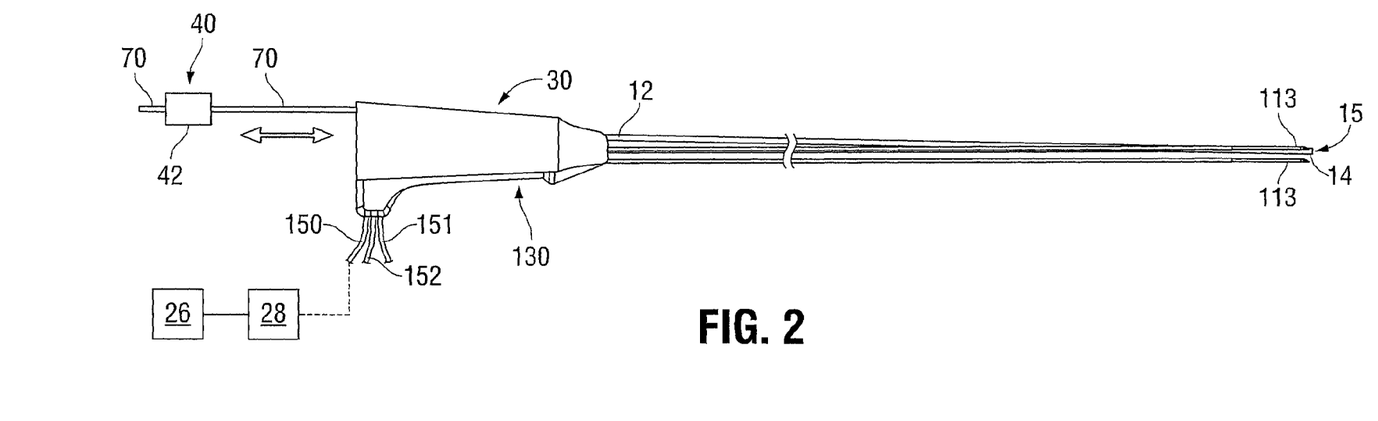
FIG. 2 is a schematic view of the drug-delivery device of FIG. 1 coupled to an energy-delivery device, such as the energy-delivery device of FIG. 1, showing the drug-delivery device in a first configuration in which the knob member thereof is disposed in a proximal position, wherein the drug-delivery lumen is configured in a retracted position, in accordance with an embodiment of the present disclosure.

In some embodiments, as shown in FIGS. 2 and 3, the drug-delivery device 10 is adapted to allow the user to selectively position the distal portion 74 of the delivery lumen 70 from at least a first configuration, wherein the distal portion 74 of the delivery lumen 70 is positioned proximal to the distal end portion 113 of the ablation electrodes 110, to at least a second configuration, wherein at least a portion of the distal portion 74 of the delivery lumen 70 is positioned distally beyond the distal end portion 113 of the ablation electrodes 110.

As shown in FIGS. 2 and 3, knob member 42 is selectively moveable from at least a first configuration, wherein the distal portion 74 of the delivery lumen 70 is positioned proximal to the distal end 14 of the shaft portion 12 (FIG. 2), to at least a second configuration, wherein at least a portion of the distal portion 74 of the delivery lumen 70 is positioned distally beyond the distal end 14 of the shaft portion 12 (FIG. 3).

Figure 4:
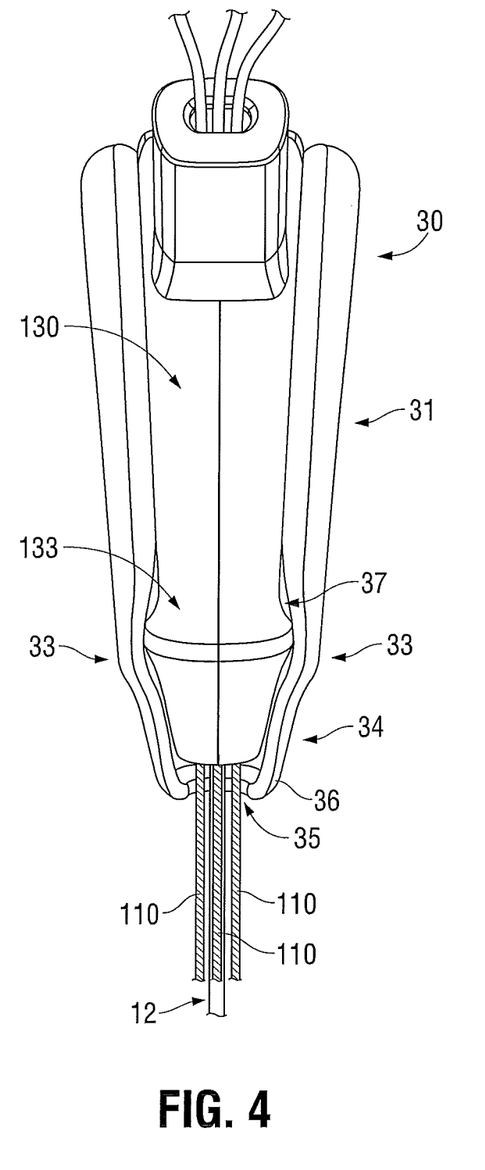
FIG. 4 is a bottom, perspective view of the drug-delivery device of FIG. 2 coupled to an energy-delivery device, in accordance with an embodiment of the present disclosure.

Drug-delivery device 10 includes a body 30 configured to be attachable to an energy-delivery device (e.g., ablation device 101 shown in FIG. 1). Body 30 may have various configurations. As seen in FIGS. 1 and 4, body 30 includes a proximal portion 31, a distal portion 34, and a contoured portion 33 disposed between the proximal and distal portions 31 and 34, respectively. As best seen in FIG. 4, the contoured portion 33 of the body 30 is configured to engage with a contoured portion 133 of the ablation device 101.

Body 30 defines a body chamber 37 therein (FIG. 4) having an interior space configured to accommodate one or more components of the ablation device 101, e.g., a handle (e.g., handle assembly 130 shown in FIG. 1) or portion thereof. In some embodiments, the body 30 may include one or more internal walls (not shown) configured to partition the body chamber 37 into one or more compartments. Body 30 may additionally, or alternatively, include an actuator (not shown), such as a slideably moveable member, e.g., thumb-slide actuator, adapted to allow the user to selectively initiate/activate the delivery of drug and/or contrast agent through the delivery lumen 70 to the tissue site.

Body 30 may be formed of any suitable material or combination of materials by any suitable process. In some embodiments, the drug-delivery device 10 may be adapted to be a reusable device. Autoclavable materials may be used to form the body 30, and/or other components of the drug-delivery device 10, to provide for a sterilizable device. Body 30, or portions thereof, may be formed from two housing halves (not shown). Each half of the housing may include a series of mechanical interfacing components (not shown) configured to matingly engage with a corresponding series of mechanical interfaces (not shown) to align the two housing halves to define therein the body chamber 37. It is contemplated that the housing halves (as well as other components described herein) may be assembled together with the aid of alignment pins, snap-like interfaces, tongue and groove interfaces, locking tabs, adhesive ports, etc., utilized either alone or in combination for assembly purposes.

In some embodiments, as shown in FIG. 6, the body 30 is configured to provide support for the shaft portion 12 wherein the shaft portion 12 extends distally from the body 30 at a predetermined angle, e.g., relative to a longitudinal axis of the body 30, whereby the distal end 14 of the shaft portion 12 is disposed within the perimeter defined by the distal end portion 113 of the three ablation electrodes 110.

Figure 7:
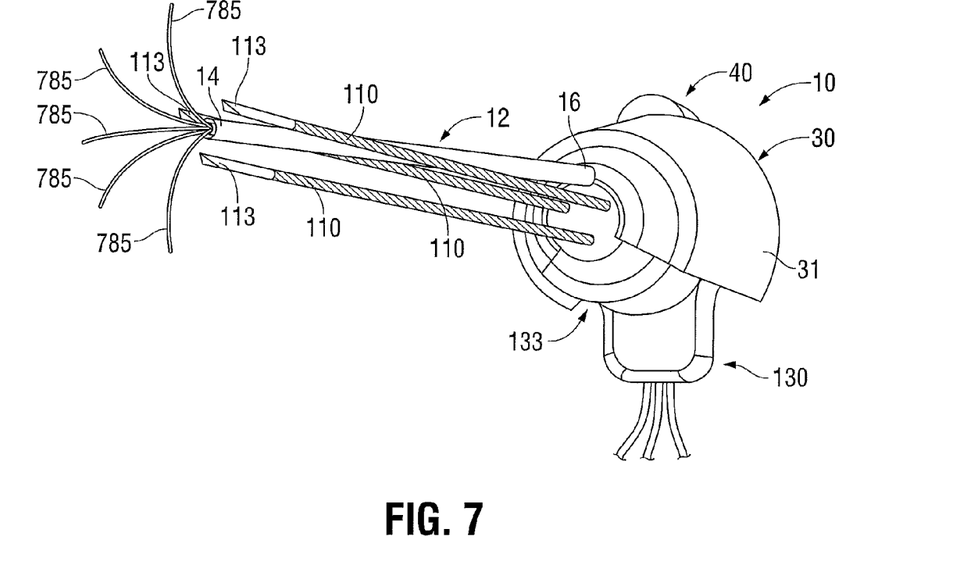
FIG. 7 is a side, perspective view of the energy-delivery device and the drug-delivery device of FIG. 1, illustrating an alternative embodiment of the drug-delivery lumen thereof, shown in an extended position, in accordance with the present disclosure.
Figure 8:
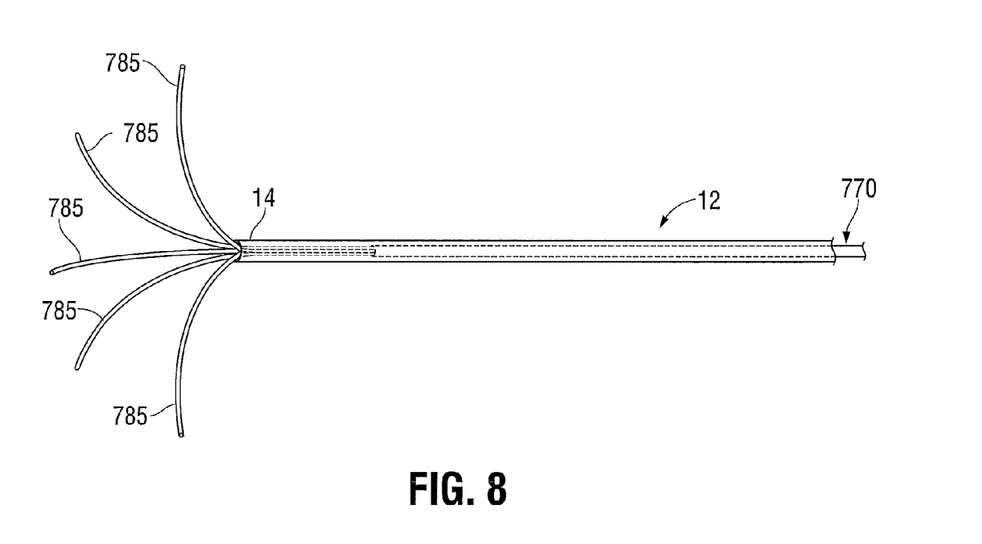
FIG. 8 is an enlarged view of the distal portion of the drug-delivery lumen of the drug-delivery device of FIG. 7 shown extending outwardly from the distal end of the shaft.

FIG. 7 shows the drug-delivery device 30 of FIG. 1 including an alternative embodiment of the drug-delivery lumen (shown as 70 in FIG. 1), shown in an extended position. The drug-delivery lumen 770 shown in FIGS. 7 and 8 includes a multi-lumen configuration. As best seen in FIG. 8, the drug-delivery lumen 770 includes five lumens 785, shown extending outwardly of the distal end 14 of the shaft portion 12. The shape, size and number of lumens 785 of the drug-delivery lumen 770 may be varied from the configuration depicted in FIGS. 7 and 8.

Figure 9:
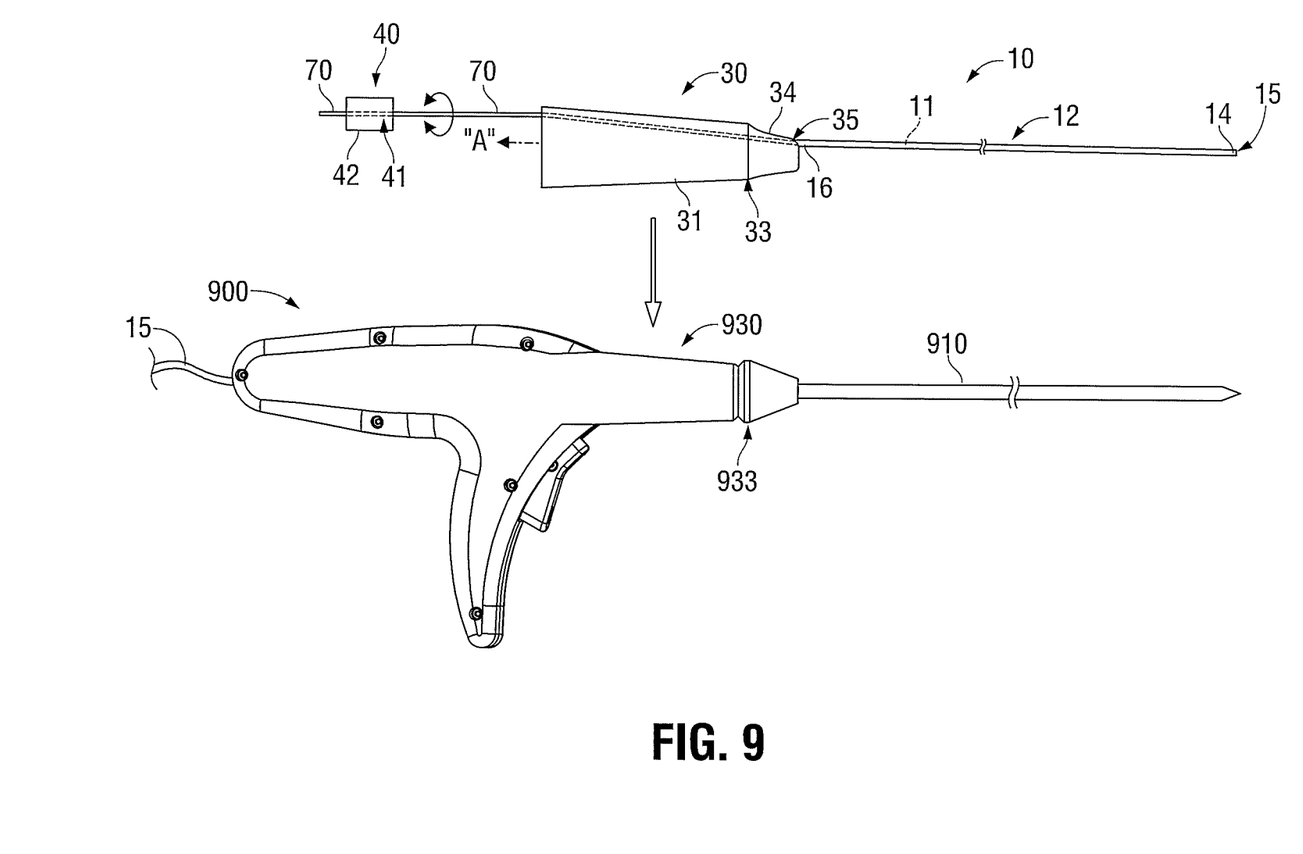
FIG. 9 is a schematic view of the drug-delivery device of FIG. 1 in an aligned position with respect to another embodiment of an energy-delivery device, spaced apart therefrom, in accordance with an embodiment of the present disclosure.

FIG. 9 shows the drug-delivery device 10 of FIG. 1 and an ablation device 900. Ablation device 900 includes a microwave probe 910 and a handle assembly 930. Ablation device 900 is configured to be operatively connected via a transmission line 15 to an electrosurgical power generating source (not shown in FIG. 9), e.g., a microwave electrosurgical generator.

Drug-delivery device 10 includes a body 30 configured to be attachable to an energy-delivery device (e.g., ablation device 900 shown in FIG. 9, or ablation device 101 shown in FIG. 1). As seen in FIG. 9, the contoured portion 33 of the body 30 of the drug-delivery device 10 is configured to engage with a contoured portion 933 of the handle assembly 930 of the ablation device 900. Body 30 may have various configurations, e.g., depending upon the configuration of the handle assembly of the energy-delivery device.

A variety of drug agents may be delivered by devices according to embodiments of the present disclosure. Some examples of drug agents which may be delivered by devices according to embodiments of the present disclosure include chemotherapeutic agents such as without limitation cisplatin, paclitaxel, doxorubicin, fluorouracil, as well as other compounds such as without limitation prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropaniide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isofluorophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-oc-hydroxyprogesterone acetate, 19-nor-progesterone, norgestrel, norethindrone, norethisterone, norethiederone, progesterone, norgesterone, norethynodrel, aspirin, indornethacin, naproxen, fenoprofen, sulindac, indoprofen, nitroglycerin, isosorbide dinitrate, propranolol, timolol, atenolol, aiprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, mitrinone, capropril, mandol, quanbenz, hydrochlorothiazide, ranitidine, flurbiprofen, fenufen, fluprofen, tolmetin, alciofenac, mefenamic, flufenamic, difiuinal, nimodipine, nitrendipine, nisoldipine, nicardipine, felodipine, lidoflazine, tiapamil, gallopamul, amlodipine, mioflazine, lisinoipril, enalapril, enalaprilat, captopril, ramipril, famotidine, nizatidine, sucralfate, etintidine, tetratolol, minoxidil, chlordazepoxide, diazepam, amitriptyline, and imipramine; opioids such as meperidine, hydrocodone, oxycodone, and semi-synthetic opioids such as oxymorphone, hydromorphone, opiates such as morphine and codeine, opioid antagonists such as without limitation naltrexone, nalbuphine, naloxone as well as opioid agonist/antagonist compounds such as buprenorphine, and synthetic analgesics such as methadone, tramadol, fentanyl and sufentanil.

Some other examples of drug agents which may be delivered by devices according to embodiments of the present disclosure include vitamin and supplements such as vitamins B-12 (cyanocobalamin) and D2, anti-virals such as without limitation acyclorvir and zidovudine; proteins and peptides such as without limitation insulin, colchicine, glucagon, thyroid stimulating hormone, parathyroid and pituitary hormones, calcitonin, renin, prolactin, corticotrdphin, thyrotropic hormone, follicle stimulating hormone, chorionic gonadotropin, gonadotropin releasing hormone, bovine somatotropin, porcine somatotropin, oxytocin, vasopressin, GRE, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagulation factors, human pancreas hormone releasing factor, analogs and derivatives of these compounds, and pharmaceutically acceptable salts of these compounds, or their analogs or derivatives. On the molecular level, the various forms of the beneficial agent may include uncharged molecules, molecular complexes, and pharmaceutically acceptable acid addition and base addition salts such as hydrochlorides, hydrobromides, acetate, sulfate, laurylate, oleate, and salicylate. Examples of acidic compounds which may be delivered by devices according to embodiments of the present disclosure include salts of metals, amines or organic cations. Derivatives such as esters, ethers and amides may also be used.

A drug agent for delivery by devices according to embodiments of the present disclosure may be used alone or mixed with other agents. A drug agent for delivery by the presently-disclosed devices may include pharmaceutically acceptable excipients, polymeric carriers and/or additional ingredients, such as antioxidants, stabilizing agents, permeation enhancers, polysaccharides, proteins, nucleotides like aptamers, and fatty acids, etc., and fabricated into different forms, such as solution, suspension, gel, colloidal dispersion like liposome, or micro- and nano-particles for controlled delivery of the drug agent. A drug agent for delivery by the presently-disclosed devices may include a thermo-sensitive metal depositor or any such compound that increases the sensitivity of the target tissue, e.g., tumor, to ablation.

A drug agent for delivery by the presently-disclosed devices may include a cryoablation agent, e.g., liquid nitrogen, and may prove complementary to thermal ablation that uses electrosurgical energy at RF or microwave frequencies.

The above-described devices provide to the capability to operate with two or more different modalities (e.g., ablation and drug delivery), without any fundamental change to the device architecture, manufacturing process etc. for the ablation device.

The above-described systems and drug-delivery devices coupled to ablation devices may offer improved anti-cancer efficacy with RF ablation (or microwave ablation) and localized drug delivery capabilities integrated into a dual medical device. In accordance with the above-described systems and ablation devices, an approach is taken to deliver drug formulation(s) locally when the anatomical access has already been obtained for the purpose of RF or microwave ablation, which, in turn, presents the prospect of reduced side-effects associated with systemic administration of the same drug molecule(s).

In accordance with the above-described systems and ablation devices, heat activated drugs may be delivered to the periphery of the tumor, which may not get as hot as the center of the tumor, to ensure adequate margins. The above-described systems and ablation devices may be used to kill tumors from the inside out, wherein the temperature at the periphery may not be high enough to destroy the tumor through ablation (e.g., in some cases, requiring temperatures of at least 55° C.), but at high enough temperature (e.g., in some cases, temperatures of about 45° C.) to activate one or more drugs delivered by the above-described ablation devices, which may take care of killing the tumor edges.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical system, comprising:
   an ablation device including a handle portion and a plurality of ablation electrodes operatively connected to the handle portion, wherein the handle portion includes a contoured portion; and
   a drug-delivery device, including:
      a body configured for attachment to the handle portion of the ablation device, the body including a proximal portion, a distal portion, and a contoured portion disposed therebetween, wherein the contoured portion of the body is configured for engagement with the contoured portion of the handle portion of the ablation device;
      a shaft defining a passageway therein, the shaft including a proximal end and a distal end, wherein the proximal end of the shaft is attached to an opening defined in the distal end of the body;
      a delivery lumen for drug delivery to tissue, the delivery lumen including a proximal portion and a distal portion, wherein the passageway of the shaft is configured to receive the delivery lumen slideably moveably therein; and
      a knob member coupled to the proximal portion of the delivery lumen.

2. The electrosurgical system of claim 1, wherein the body of the drug-delivery device is configured to provide support for the shaft such that the shaft extends distally from the body at a predetermined angle.

3. The electrosurgical system of claim 2, wherein the distal end of the shaft is disposed within a perimeter defined by a distal end portion of the plurality of ablation electrodes.

4. The electrosurgical system of claim 1, wherein the knob member of the drug-delivery device is selectively moveable from at least a first configuration, wherein the distal portion of the delivery lumen is positioned proximal to the distal end of the shaft, to at least a second configuration, wherein at least a portion of the distal portion of the delivery lumen is positioned distally beyond the distal end of the shaft.

* * * * *